(12) United States Patent
Platt et al.

(10) Patent No.: US 6,291,657 B1
(45) Date of Patent: Sep. 18, 2001

(54) DEOXYGALACTONOJIRIMYCIN DERIVATIVES

(75) Inventors: Frances M. Platt, Oxford (GB); Gabrielle R. Neises, Chesterfield, MO (US); Raymond A. Dwek; Terry D. Butters, both of Oxford (GB)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 08/102,654

(22) Filed: Aug. 5, 1993

Related U.S. Application Data

(63) Continuation-in-part of application No. 08/061,645, filed on May 13, 1993, now Pat. No. 5,399,567.

(51) Int. Cl.$^7$ .................................................. C07H 15/00
(52) U.S. Cl. .............................................. 536/17.2; 536/4.1
(58) Field of Search .............................. 514/315; 536/4.1, 536/17.2

(56) References Cited

U.S. PATENT DOCUMENTS

| | | | |
|---|---|---|---|
| 4,065,562 | 12/1977 | Ohata et al. ........................ | 424/267 |
| 4,182,767 | 1/1980 | Murai et al. ........................ | 424/267 |
| 4,533,668 | 8/1985 | Matsumara et al. ................ | 514/321 |
| 4,639,436 | 1/1987 | Junge et al. ......................... | 514/24 |
| 4,849,430 | 7/1989 | Fleet et al. .......................... | 514/315 |
| 5,011,829 | * 4/1991 | Hirsch ................................. | 514/50 |
| 5,030,638 | 7/1991 | Partis et al. ......................... | 514/315 |
| 5,128,347 | * 7/1992 | Getman .............................. | 514/32 |

FOREIGN PATENT DOCUMENTS

| | | | |
|---|---|---|---|
| 536402 | 4/1993 | (EP) ........................ | C07D/211/46 |
| 8703903 | 7/1987 | (WO) . | |

OTHER PUBLICATIONS

Merck Manual, p 106–108, 978–979 1982.*
Chem Abst. 115(13) 136547 of J. Am Chem. Soc. 113(17):6678–80 1991.*
Saunier et al., J. Biol. Chem. 257, 14155–14161 (1982).
Elbein, Ann. Rev. Biochem. 56, 497–534 (1987).
NewBrun, Arch. Oral Biol. 28, 531–536 (1982).
Wang et al., Tetrahedron Lett. 34, 403–406 (1993).
Karlsson et al., J. Biol. Chem. 268, 570–576 (1993).
Legler & Pohl, Carb. Res. 155, 119 (1986).
Beutler, Science 256, 794–799 (1992).
Beutler, Proc. Natl. Acad. Sci. USA, 5384–5390 (1993).
Fleet et al., FEBS. Lett. 237, 128–132 (1988).
van Heyningen, Nature 249, 415–417 (1979).
Karlsson, Ann. Rev. Biochem. 58, 309–350 (1989).
Platt et al., Eur. J. Biochem. 208, 187–193 (1992).
Butters and Hughes, In Vitro 17, 831–838 (1981).

* cited by examiner

*Primary Examiner*—Elli Peselev
(74) *Attorney, Agent, or Firm*—Scott J. Meyer

(57) ABSTRACT

Novel N-alkyl derivatives of deoxygalactonojirimycin are provided in which said alkyl contains from 3–6 carbon atoms. These novel compounds are useful for selectively inhibiting glycolipid synthesis.

1 Claim, 11 Drawing Sheets

US 6,291,657 B1

DEOXYGALACTONOJIRIMYCIN DERIVATIVES

CROSS-REFERENCE TO RELATED APPLICATION

This application is a continuation-in-part of copending application Ser. No. 08/061,645, filed May 13, 1993 now U.S. Pat. No. 5,399,567.

BACKGROUND OF THE INVENTION

This invention relates to novel N-alkyl derivatives of deoxygalactonojirimycin (DGJ) in which said alkyl groups contain from 3–6 carbon atoms. These novel compounds are useful for selectively inhibiting glycolipid synthesis.

In applicants' copending application Ser. No. 08/061,645, filed May 13, 1993, now U.S. Pat. No. 5,399,567 certain N-alkyl derivatives of deoxynojirimycin (DNJ) are disclosed as effective inhibitors of glycolipid biosynthesis. N-alkylated derivatives of DNJ were also previously known to be inhibitors of the N-linked oligosaccharide processing enzymes, α-glucosidase I and II. Saunier et al., *J. Biol. Chem.* 257, 14155–14166 (1982); Elbein, *Ann. Rev. Biochem.* 56, 497–534 (1987). As glucose analogues, they also have potential to inhibit glucosyltransferases. Newbrun et al., *Arch. Oral Biol.* 28, 516–536 (1983); Wang et al., *Tetrahedron Lett.* 34, 403–406 (1993). Their inhibitory activity against the glucosidases has led to the development of these compounds as antihyperglycemic agents and antiviral agents. See, e.g., PCT Int'l. Appln. WO 87/03903 and U.S. Pat. Nos.: 4,065,562; 4,182,767; 4,533,668; 4,639,436; 4,849,430; 5,011,829; and 5,030,638.

BRIEF DESCRIPTION OF THE INVENTION

In accordance with the present invention, novel N-alkyl derivatives of deoxygalactonojirimycin (DGJ) are provided in which said alkyl contains from 3–6 carbon atoms and preferably from 4–6 carbon atoms. These novel compounds are useful for selectively inhibiting glycolipid synthesis. The length of the N-alkyl chain has been found to be important to said inhibitory activity since the non-alkylated DGJ and the N-methyl and N-ethyl derivatives of DGJ were each found to be inactive for such inhibition. The N-propyl derivative of DGJ was partially active. Thus, a minimum alkyl chain length of 3 carbon atoms has been found to be essential for efficacy.

The biosynthesis of glycolipids in cells capable of producing glycolipids can be selectively inhibited by treating said cells with a glycolipid inhibitory effective amount of an N-alkyl derivative of DGJ of the present invention. These inhibitory compounds can be used at concentrations of about 10-fold less than the effective antiviral concentrations of the corresponding N-alkyl derivatives of DNJ. Illustratively, the N-butyl DGJ is inhibitory of glycolipid biosynthesis at relatively low concentration of about 50 μM compared to the 0.5 mM level of concentration of N-butyl DNJ in cell culture systems for α-glucosidase I inhibition (Karlsson et al., *J. Biol. Chem.* 268, 570–576 (1993).

The active N-alkyl derivatives of DGJ have a significant advantage since, unlike the previously described N-alkyl derivatives of DNJ, they selectively inhibit biosynthesis of glycolipids without effect either on the maturation of N-linked oligosaccharides or lysosomal glucocerebrosidase. For example, in contrast to N-butyl DNJ, the N-butyl DGJ of the present invention surprisingly does not inhibit the processing α-glucosidases I and II or lysosomal β-glucocerobrosidase. Likewise, the only prior reported experimental evidence using deoxygalactonojirimycin indicates that N-alkylation (N-heptyldeoxygalactonojirimycin) provides a modest increase in the affinity towards certain β-glucosidases [Legler & Pohl, Carb. Res. 155, 119 (1986)]. The inhibitory results described herein for the novel N-alkylated deoxygalactonojirimycin analogues in which the alkyl contains from 3 to 6 carbon atoms were unexpected in view of the corresponding activity of related iminosugar compounds.

Further uniqueness of the present invention is seen by the finding that the exemplary N-butyl and N-hexyl derivatives of DGJ completely prevented glycolipid biosynthesis, whereas the N-butyl derivatives of mannose, fucose and N-acetylglucosamine were without effect on glycolipid biosynthesis.

The inhibitory effect of these compounds on the biosynthesis of glycolipids is illustrated herein in the myeloid cell line HL-60 and in the lymphoid cell line H9. These are well-known, widely distributed and readily available human cell lines. For example, HL-60 cells are promyelocitic cells described by Collins et al., *Nature* 270, 347–349 (1977). They are also readily available from the American Type Culture Collection, Rockville, Md, U.S.A., under accession number ATCC CCL 240. H9 cells are of lymphoid origin described by Gallo and Popovic, *Science* 224, 497–500 (1984). They are also readily available from the same depository under accession number ATCC HTB 176.

The inhibition of glycolipid biosynthesis by these N-alkyl derivatives of DGJ is further demonstrated herein by the reduction of the binding of cholera toxin to the illustrative cell line H9 when cultured in the presence on N-butyl DGJ. These compounds thus are also useful as anti-microbial agents by inhibiting the and bacterial toxins as illustrated hereinafter in Tables 1 and 2, respectively.

The inhibitory effect upon the biosynthesis of glycolipids is further illustrated by the ability of the N-butyl and N-hexyl derivatives of DGJ to offset glucoceramide accumulation in a standard, state-of-the-art in vitro model of Gaucher's disease. In this model, the murine macrophage cell line WEHI-3B was cultured in the presence of an irreversible glucocerebrosidase inhibitor, conduritol β epoxide (CBE), to mimic the inherited disorder found in Gaucher's disease. WEHI-3B cells are well-known, widely distributed and readily available murine macrophage cells. They are described in *Cancer Res.* 37, 546–550 (1977), and are readily available from the American Type Culture Collection, Rockville, Md, under accession number ATCC TIB 68. The compounds of the invention prevent lysosomal glycolipid storage which is useful for the management of Gaucher's disease and other glycolipid storage disorders as illustrated hereinafter in Table 3. Gaucher's disease is an autosomal recessive disorder characterized by an impaired ability to degrade glucocerebroside (glucosyl ceramide, Glc-Cer) due to mutations in the gene encoding β-glucocerebrosidase (β-D-glucosyl-N-acylsphingosine glucohydrolase, EC 3.2.1.45). This defect results in the lysosomal accumulation of Glc-Cer in cells of the macrophage-monocyte system [Barranger and Ginns, in *The Metabolic Basis of Inherited Diseases*, ed. Scriver et al., pp. 1677–1698, McGraw-Hill, New York, (1989); Beutler, *Science* 256, 794–799 (1992)]. By slowing the rate of glycolipid synthesis, the impaired catabolism of Glc-Cer can be offset, thereby leading to the maintenance of a balanced level of Glc-Cer.

The clinical management of Gaucher's disease currently relies upon either symptomatic treatment of patients or enzyme replacement therapy [Beutler, *Proc. Natl. Acad. Sci. USA* 90, 5384–5390 (1993)]. In view of the prohibitive cost of enzyme replacement therapy and the requirement for intravenous administration of glucocerebrosidase, an orally available alternative therapy based around substrate deprivation constitutes a useful alternative. The N-alkyl derivatives of DGJ are water-soluble sugar analogs and, therefore, orally active. Since the N-alkyl DGJ compounds exhibit fewer complicating enzyme inhibitory characteristics than α-and β-glucosidase inhibitors, they also constitute a preferable alternative to the N-alkyl DNJ compounds for therapeutic management of Gaucher's disease and other glycolipid storage disorders. The N-alkyl DGJ may also be used in combination with glucocerebrosidase for the treatment of Gaucher's disease.

DETAILED DESCRIPTION OF THE INVENTION

While the specification concludes with claims particularly pointing out and distinctly claiming the subject matter regarded as forming the invention, it is believed that the invention will be better understood from the following illustrative detailed description of the invention taken in conjunction with the accompanying drawings in which:

FIG. 1 shows by one dimensional thin layer chromatography (1D-TLC) a comparison of N-alkylated imino sugars as inhibitors of glycolipid biosynthesis. 1D-TLC separation was made of HL-60 total cellular lipids labelled with [$^{14}$C]-palmitic acid. Cells were treated with either 0.5 mM N-butyl deoxynojirimycin (NB-DNJ), N-butyl deoxymannojirimycin (NB-DMJ), N-butyl deoxygalactonojirimycin (NB-DGJ) or N-butyl 2-acetamido-1,2,5-trideoxy-1,5-imino-D-glucitol (NB-NAG) or untreated (UT). Glycolipid biosynthesis inhibition was detected by the lack of Glc-Cer, gangliosides and an unknown species (indicated with arrows). Glc-Cer migration was confirmed by inclusion of a [$^{14}$C]-Glc-Cer standard on the TLC. The radiolabelled lipid species were visualized by autoradiography.

FIG. 2, in three parts, A, B and C, shows 2D-TLC analysis of HL-60 cells treated with either NB-DNJ or NB-DGJ. 2D-TLC separation was made of total HL-60 lipids labelled with [$^{14}$C]-palmitic acid. Cells were treated with either 0.5 mM NB-DNJ or NB-DGJ or untreated (UT). Lipids were assigned as follows (untreated cells, lefthand panel, FIG. 2A): 1, gangliosides; 2, lysophospatidylcholine; 3, ceramide phosphorylcholine; 4, ceramide phosphorylethanolamine; 5, phospatidylcholine; 6, phosphatidylinositol; 7, phosphatidylethanolamine; 8, phosphatidylglycerol; 9, diglycosylceramide; 10, monoglycosylceramide; 11, cholesterol/fatty acids/neutral lipids; N and N* are unknowns; and 0 is the sample origin. Following NB-DNJ and NB-DGJ treatment (middle and righthand panels, FIGS. 2B and 2C, respectively) species 1 (gangliosides); 9 (diglycosylceramide); 10 (monoglycosylceramide) and N* (unknown) were absent. The radiolabelled lipids were visualized by autoradiography.

FIG. 3 shows the dose dependent effects of NB-DNJ and NB-DGJ on glycolipid biosynthesis. 1D-TLC analysis was made of total cellular lipids. HL-60 cells were labelled with [$^{14}$C]-palmitic acid in the presence or absence (UT) of NB-DNJ or NB-DGJ at the indicated concentrations (μM). The migration position of [$^{14}$C]-Glc-Cer is indicated by arrows. The lipids were visualized by autoradiography.

FIG. 4, in two parts, A and B, shows the effects of increasing DNJ and DGJ N-alkyl chain length on inhibition of glycolipid biosynthesis. 1D-TLC analysis was made of total cellular lipids. HL-60 cells were treated with [$^{14}$C]-palmitic acid in the presence or absence (UT) of either DNJ, or the N-ethyl, N-methyl, N-propyl, N-butyl and N-hexyl derivatives of DNJ (lefthand panel, FIG. 4A) or DGJ, or the N-ethyl, N-methyl, N-propyl, N-butyl and N-hexyl derivatives of DGJ (righthand panel, FIG. 4B) at 0.5 mM concentration. The migration position of [$^{14}$C]-Glc-Cer is indicated with arrows. The lipids were visualized by autoradiography.

FIGS. 5 and 6 show the analysis of NB-DNJ and NB-DGJ in an in vitro Gaucher's disease model. Specifically, FIG. 5 shows the 1D-TLC analysis of glycolipids from WEHI-3B cells treated with either NB-DNJ or NB-DGJ, at the indicated concentrations (AM), and visualized by chemical detection (see methods hereinafter).

FIG. 6, in eight parts, A through H, shows the transmission electron microscopy of WEHI-3B cell lysosomes: FIG. 6A, untreated; FIG. 6B, conduritol β epoxide (CBE) treated; FIG. 6C, CBE and 500 μM NB-DNJ; FIG. 6E, CBE and 50 μM NB-DNJ; FIG. 6G, CBE and 5 μM NB-DNJ; FIG. 6D, CBE and 500 μM NB-DGJ; FIG. 6F, CBE and 50 μM NB-DGJ; FIG. 6H, CBE and 5 μM NB-DGJ. The scale bar at the lower right hand corner of FIG. 6H is applicable to all of FIGS. 6A through H and represents 0.1 μM.

FIG. 7 shows the effect of NB-DGJ on N-linked oligosaccharide processing. Specifically, it shows Endo H sensitivity of gp120 expressed in Chinese hamster ovary (CHO) cells in the presence or absence (−) of either NB-DNJ or NB-DGJ (0.5 mM and 5 mM). The arrows indicate the molecular weight of the untreated gp120 (120 kDa) and post endo H digestion (60 kDa). An additional band of low molecular weight (approximately 60 kDa) was present in some lanes and is a non-specific protein precipitated by the solid phase matrix.

FIG. 8 is a graphical representation that shows, in three parts, A, B and C, the effect of imino sugar analogues on glycolipid and glycoprotein metabolizing enzyme activity. Enzyme activity was determined in the presence of the following test compounds: DNJ, (♦); NB-DNJ, (■); DGJ, (▲); NB-DGJ, (●) at concentrations shown (see methods hereinafter). FIG. 8A, UDP-glucose:N-acylsphingosine glucosyltransferase; FIG. 8B, β-glucocerebrosidase; FIG. 8C, processing α-glucosidase. Enzymatic activity is expressed as a percentage of control reactions that contained no test compound.

Figure 11:
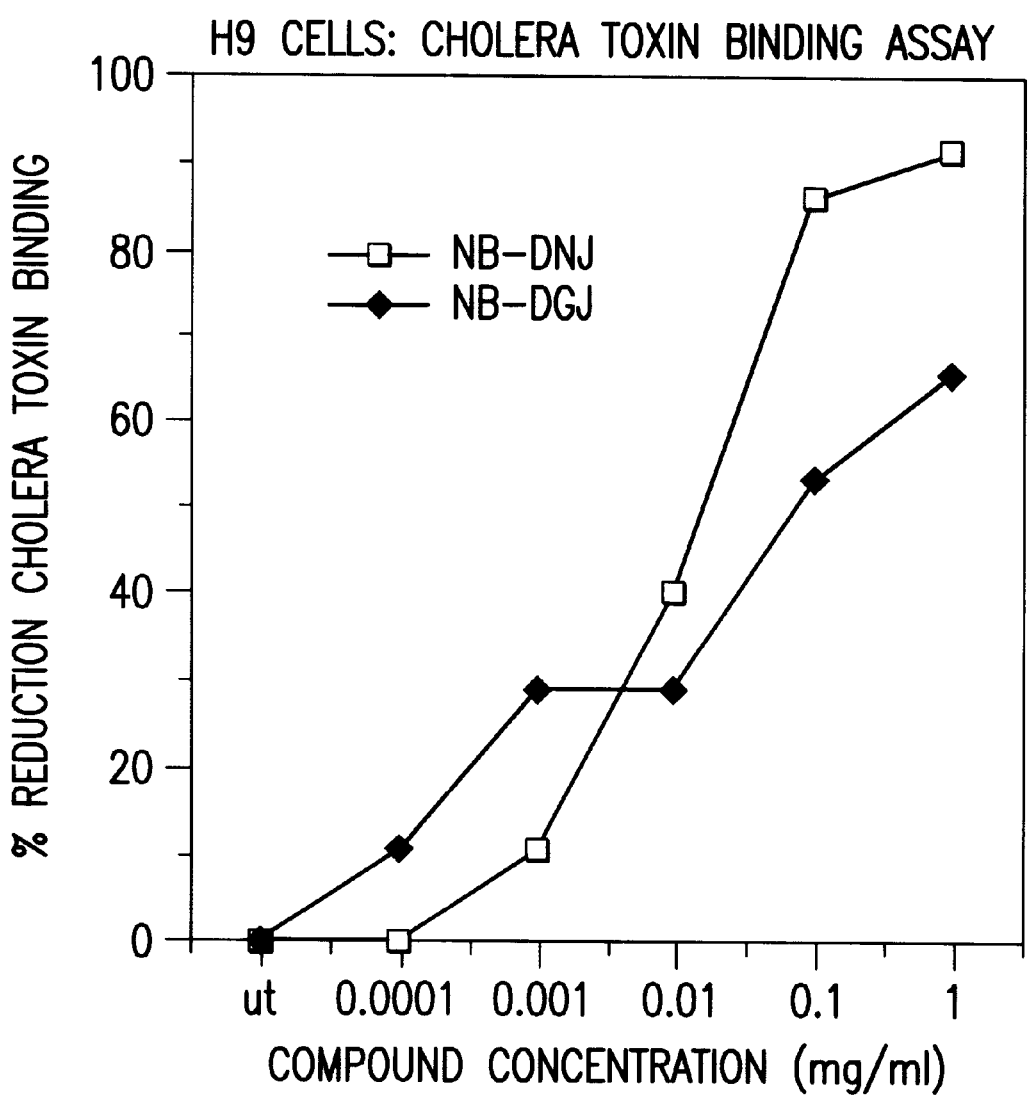

FIG. 11 is a graphical representation of a cholera toxin binding assay and shows on the y-axis the % reduction in cholera toxin binding sites per cell for H9 cells in which the cholera toxin was fluorescein conjugated and in which the levels of binding to the cell surfaces of untreated (ut) cells and cells treated with N-butyl deoxygalactonojirimycin (NB-DGJ) or, for comparison, N-butyl deoxynojirimycin (NB-DNJ), at various levels shown on the x-axis (mg/ml), were measured by flow cytometry.

In order to further illustrate the invention, the following detailed examples were carried out although it will be understood that the invention is not limited to these specific examples or the details therein.

EXAMPLES

MATERIALS & METHODS

Compounds:

N-Butyldeoxynojirimycin (NB-DNJ) was obtained from Searle/Monsanto (St. Louis, Mo., U.S.A.). Deoxygalactonojirimycin (DGJ), deoxyfuconojirimycin (DFJ), deoxymannojirimycin (DMJ), and 2-acetamido-1,2,5-trideoxy-1,5-imino-D-glucitol (NAG), were obtained from Cambridge Research Biochemicals (Northwich, Cheshire, U.K.). DGJ, DFJ, DMJ and NAG were reductively N-alkylated in the presence of palladium black under hydrogen using the appropriate aldehyde by conventional procedure as described by Fleet et al., *FEBS Lett.* 237, 128–132 (1988). The reaction mixture was filtered through Celite and the solvent removed by evaporation under vacuum. The resulting N-alkylated analogues were purified by ion-exchange chromatography (DOWEX® AG50-X12, H+ form) in 2M $NH_3$ (aq) and the solvent removed by evaporation. These compounds were lyophilised and analysed by 1D $^1H$ NMR at 500 MHz on a Varian Unity 500 spectrophotometer and by matrix assisted laser desorption (Finnegan). All compounds synthesised were greater than 95% pure. The following are representative examples of the synthesis of the foregoing N-alkylated compounds as used hereinafter.

Example 1

Figure 9:
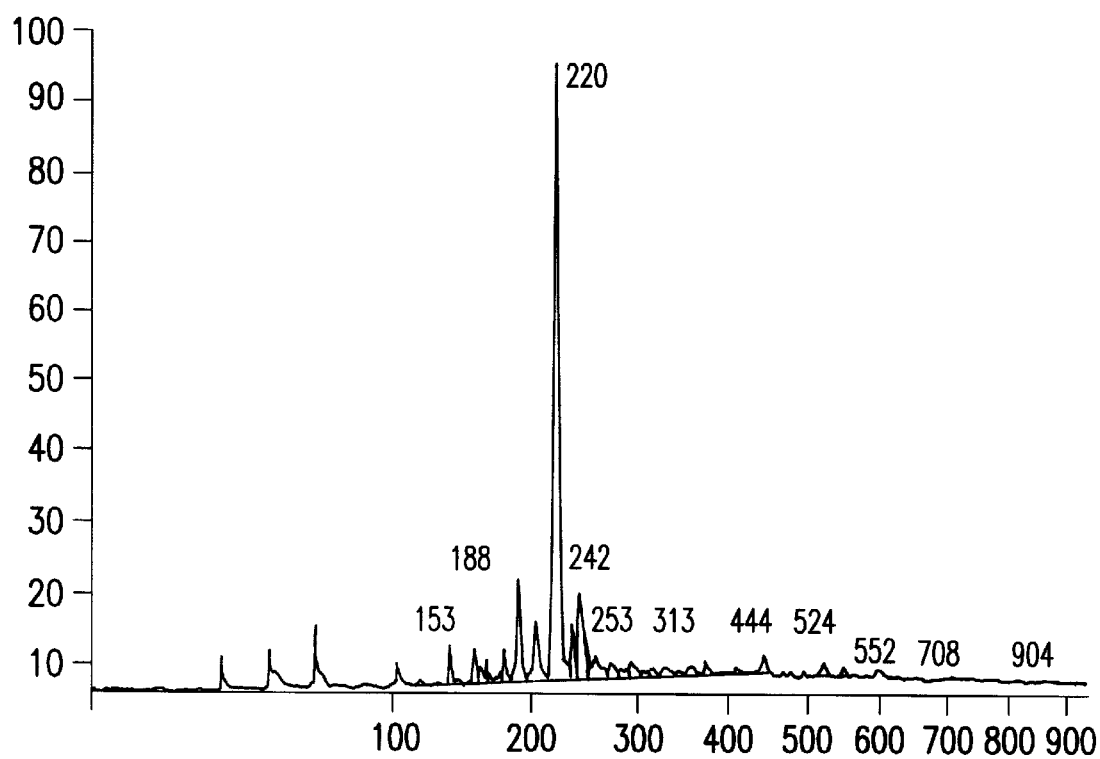
FIG. 9 shows the laser desorption mass spectrometry of N-butyl deoxygalactonojirimycin with a molecular weight of 220 (M+H) and obtained in greater than 95% purity.
Figure 10:
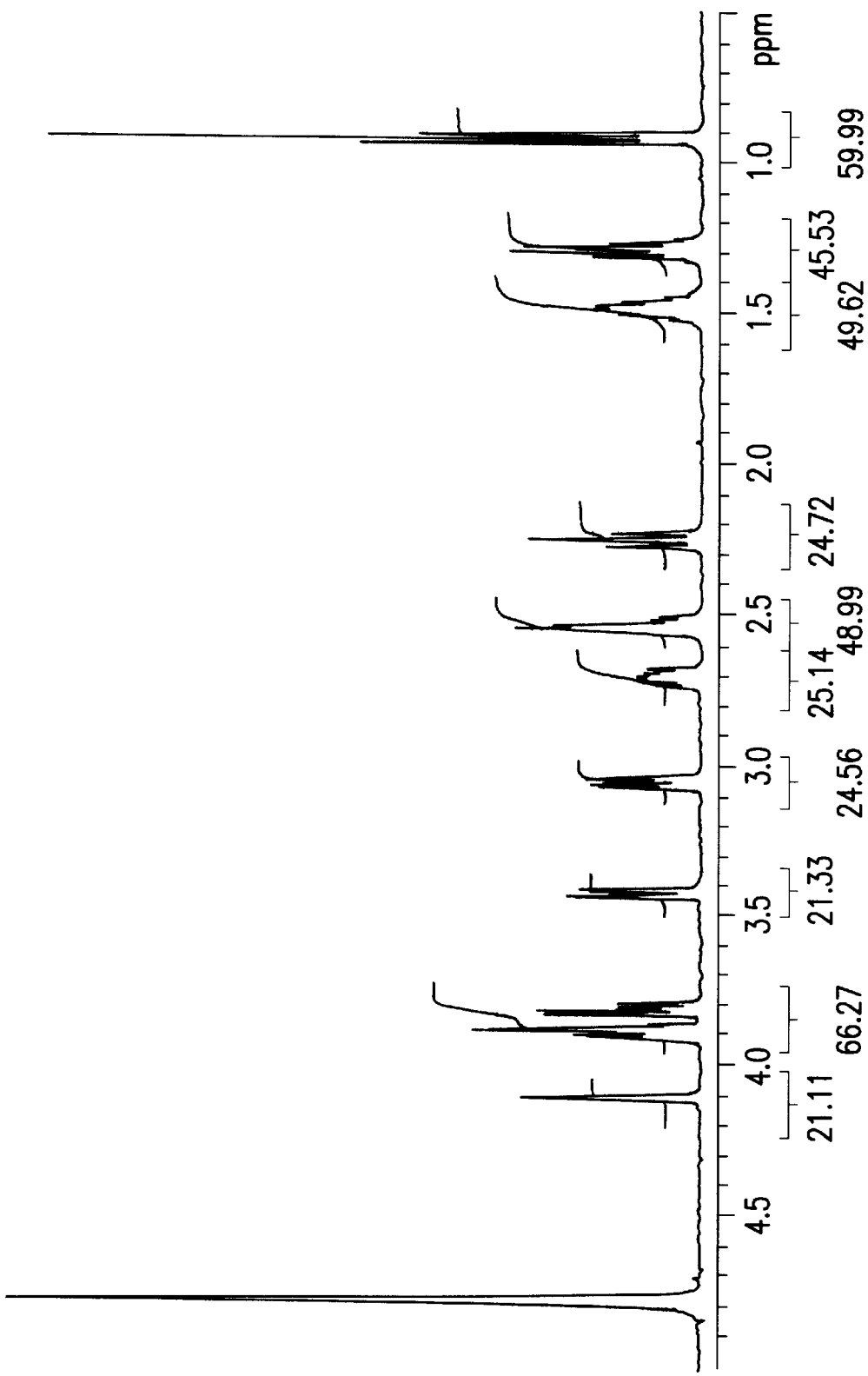
FIG. 10 shows the $^1$H NMR spectrum of N-butyl deoxygalactonojirimycin.

In a representative example of the preparation of the N-butyl deoxygalactonojirimycin, 30 mg (184 μmol) of deoxygalactonojirimycin was dissolved in 1 ml of 50 mM sodium acetate buffer, pH 5.0, to which 20 mg of palladium black was added. A hydrogen atmosphere was maintained in the reaction vessel and 100 μl (1.1 mmol) of butyraldehyde was introduced. The reaction was stirred for 16 hr. at room temperature (ca. 20° C.). The reaction was stopped by filtration through a bed (1 g) of Celite (30–80 mesh) and the reaction products were separated by chromatography using a column containing 4 ml of packed DOWEX® AG50-X12 (H+ form) resin. The N-butyl deoxygalactonojirimycin was eluted from the chromatography column with 2M ammonia. Its molecular mass was 220 (M+H) as determined by laser desorption mass spectrometry and its chemical structure was confirmed by 1D $^1H$ NMR as shown in FIGS. 9 and 10, respectively.

Example 2

The synthesis procedure and compound analysis of Example 1 was repeated except that caproaldehyde was substituted for an equivalent amount of butyraldehyde for analogous preparation of N-hexyl deoxygalactonojirimycin. Its molecular mass was 248 (M+H) as determined by laser desorption mass spectrometry and its chemical structure was confirmed by 1D $^1H$ NMR.

Example 3

The synthesis procedure and compound analysis of Example 1 was repeated except that propanoyl aldehyde was substituted for an equivalent amount of butyraldehyde for analogous preparation of N-propyl deoxygalactonojirimycin. Its molecular mass was 206 (M+H) as determined by laser desorption mass spectrometry and its chemical structure was confirmed by 1D $^1H$ NMR.

The N-alkylated deoxygalactonojirimycin compounds prepared in the foregoing illustrative Examples 1 to 3 were obtained in overall yields of 68–74% based on the starting deoxygalactonojirimycin and were greater than 95% pure.

Enzymes and Enzyme Assays:

Porcine liver α-glucosidase I and rat liver α-glucosidase II were purified to homogeneity and assayed by conventional procedure using a $[^{14}C]$-glucose labelled $Glc_3Man_9GlcNAc_2$ substrate as previously described by Karlsson et al., *J. Biol. Chem.* 268, 570–576 (1993).

β-D-Glucosyl-N-acylsphingosine glucohydrolase (glucocerebrosidase) was isolated from human placenta and purified to homogeneity according to published standard methods [Furbish et al., *Proc. Natl. Acad. Sci. USA* 74, 3560–3563 (1977); Dale and Beutler, Ibid. 73, 4672–4674 (1976)]. Glucocerebrosidase activity was measured by adding enzyme (5–50 μl) to a sonicated suspension of buffer (50 μl of 50 mM sodium citrate/sodium phosphate buffer, pH 5.0) containing glucosyl ceramide (1 mM), TRITON® X-100 non-ionic surfactant (0.25% v/v) and sodium taurodeoxycholate (0.6% v/v) that had been previously dried under nitrogen from chloroform:methanol (2:1 v/v) solutions. After incubation at 37° C. for 15–60 min., the reaction was stopped by the addition of 500 μl of chloroform:methanol and the phases separated by centrifugation. The upper phase was washed twice with Folch theoretical lower phase [Folch et al., *J. Biol. Chem.* 226, 497–509 (1957)] desalted using AG50-X12 ion-exchange resin and dried under vacuum. The reaction products were separated by high performance anion exchange chromatography (Dionex BioLC System) and detected by pulsed amperometry. The amount of enzyme-released glucose was calculated from peak areas by applying experimentally determined response factors for glucose relative to an included reference monosaccharide [Butters et al, *Biochem. J.* 279, 189–195 (1991)].

UDP-glucose:N-acylsphingosine glucosyltransferase (EC 2.4.1.80) activity was measured in rat brain homogenates and mouse macrophage tissue cultured cell (WEHI-3B) homogenates using a method adapted as follows from published conventional procedures [Vunnam and Radin, *Chem. & Phys. of Lipids* 26, 265–278 (1980); Shukla and Radin, *Arch. Biochem. Biophys.* 283, 372–378 (1990)]: Dioleoylphosphatidylcholine and cerebroside liposomes containing 200 nmol ceramides Type IV (Sigma) were added to a reaction mixture (100 μl) composed of 40 mM 2-[N-morpholino]ethanesulfonic acid (MES) buffer, pH 6.5, 5 mM $MnCl_2$, 2.5 mM $MgCl_2$, 1 mM NADH and 8 μM UDP-$[^{14}C]$-glucose (318 mCi/mmol, Amersham International, Amersham, U.K.). After incubation at 37° C. for 1–2 hr. the reaction was stopped by the addition of EDTA (25 mM) and KCl (50 mM). Radiolabelled glycolipids were extracted with 500 μl of chloroform:methanol (2:1 v/v) for 10 min. and the phases separated. The lower phase was washed twice with Folch theoretical upper phase and portions taken for scintillation counting. When imino sugars were tested for inhibitory activity, these were added at appropriate concentrations to homogenates and preincubated for 10 min. before sonication with ceramide containing liposomes. Control reactions were performed with liposomes containing no ceramide to measure the activity of transfer to endogenous acceptors.

Glycolipid Analysis:

HL-60 cells were cultured by conventional procedure as previously described by Platt et al., *Eur. J. Biochem.* 208, 187–193 (1992). HL-60 cells at $5 \times 10^4$ cells/ml were cultured in the presence or absence of imino sugars for 24 hr. For labelling, the two dimensional thin layer chromatography (2D-TLC) conventional method of Butters and Hughes was followed [In Vitro 17, 831–838 (1981)]. Briefly, $[^{14}C]$-palmitic acid (56.8 mCi/mmol, ICN/Flow) was added as a sonicated preparation in foetal calf serum (FCS, Techgen, London, U.K., 0.5 µCi/ml) and the cells cultured for a further 3 days maintaining the imino sugars in the medium. The cells were harvested, washed three times with phosphate buffered saline (PBS), extracted in 1 ml chloroform:methanol (2:1 v/v) and separated by 1 dimensional TLC, loading equal counts (1D-TLC, chloroform:methanol:water (65:25:4)). For two dimensional separations the one dimensional separation was performed as described above, the plate dried overnight under vacuum and separated in the second dimension using a solvent of tetrahydrofuran:dimethoxymethane:methanol:water (10:6:4:1). Plates were air dried and exposed to Hyperfilm-MP high performance autoradiography film (Amersham).

Cell Culture and Metabolic Labelling:

The culture of CHO cells expressing soluble recombinant gp120 (from Dr. P. Stevens, MRC AIDS Directed Programme Reagent Project) and the radiolabelling of these cells was carried out by conventional procedure as described by Karlsson et al., *J. Biol. Chem.* 268, 570–576 (1993). Briefly, CHO cells were harvested mechanically, washed three times with phosphate buffered saline, 0.1M pH 7.2 (PBS) and resuspended in methionine- and cysteine-free RPMI-1640 medium (ICN-Flow Laboratories, High Wycombe, Bucks, U.K.) supplemented with 1% dialysed FCS. Cells ($10^7$/ml) were preincubated in the presence or absence of NB-DNJ or NB-DGJ for 1 hr prior to the addition of 100 µCi/ml Tran$^{35}$S-label (ICN-Flow) for 4 hr. The supernatants were collected and concentrated tenfold using a 30 kDa cut-off membrane (Amicon, Danvers, Mass., U.S.A.).

Immunoprecipitation:

Immunoprecipitations were performed by conventional procedure as described by Karlsson supra. Supernatants were incubated with the mAb ABT 1001 monoclonal antibody (American Biotechnologies Inc., Cambridge, Mass., U.S.A.) at 0.5 µg/100 µl of supernatant for 30 min. at room temperature followed by sheep anti-mouse IgG1-coated magnetic beads (Dynal Ltd., Wirral, Merseyside, U.K., $1.2 \times 10^7$ beads per sample) for 1 hr. at 4° C. The beads were washed three times with 2% TRITON® X-100 in PBS and three times with PBS. Gp120 was eluted in 100 µl reducing SDS-PAGE sample buffer with heating (95° C., 5 min.). Each sample was divided into two equal aliquots and 25 µl of dH$_2$O added to give a final volume of 50 µl. To one half of each sample 2 µl of endoglycosidase H (endo H, 1 unit/ml, Boehringer Mannheim Ltd., Lewes, Sussex, U.K.) was added and the other half left untreated. Digestion was performed at 37° C. for 18 hr. and terminated by the addition of 50 µl of SDS-PAGE reducing sample buffer (95° C., 5 min.).

Glycopeptide Analysis:

HL-60 and BW5147 cells were cultured in RPMI-1640 and 10% FCS. The cells were incubated for 30 min. in the presence or absence of 2 mM NB-DNJ or NB-DGJ in reduced glucose RPMI-1640 medium (Flow), supplemented with 1% dialysed FCS. [$^3$H]-mannose (16.5 Ci/mmol, Amersham) was added at 200 µCi/ml and the cells cultured for a further 3 hr. Washed cell pellets were resuspended in 50 mM TrisHCl buffer, pH 7.5, containing 10 mM CaCl$_2$ and 0.02% sodium azide and heated at 100° C. for 5 min. After cooling, Pronase® enzyme was added to 0.04% (w/v final concentration) and incubated for 96 hr. at 37° C. under toluene with aliquots of Pronase® added at each 24 hr. period. The digestion was stopped by boiling for 5 min., and glycopeptides recovered by centrifugation at 13000 g for 10 min. Samples were fractionated by Con A-SEPHAROSE® chromatography according to conventional procedure of Foddy et al., *Biochem. J.* 233, 697–706 (1986).

In Vitro Gaucher's Disease Model:

The in vitro Gaucher's disease model was prepared as follows: WEHI-3B cells (American Type Culture Collection, Rockville, Md., U.S.A.) were maintained in logarithmic phase growth for 14 days in RPMI-1640 medium, 10% FCS, in the presence or absence of 50 µM conduritol β epoxide (CBE, Toronto Research Chemicals, Downsview, Canada) with or without NB-DNJ or NB-DGJ. Cells were passaged every 3 days and compound concentrations maintained throughout. Equal cell numbers ($5 \times 10^6$) were harvested, extracted in 1 ml chloroform: methanol (2:1 v/v) overnight at 4° C., the extracts centrifuged, the chloroform:methanol extract retained and the pellet re-extracted as above for 2 hr. at room temperature. Pooled extracts were dried under nitrogen, re-dissolved in 10 µl chloroform:methanol (2:1 v/v) and separated by 1D-TLC in chloroform:methanol:water (10:6:4:1). Plates were air dried and visualized using α-naphthol (1% w/v in methanol) followed by 50% (v/v) sulphuric acid.

Transmission Electron Microscopy:

Cells for electron microscopy were harvested ($1 \times 10^7$ cells per treatment), washed three times in serum free RPMI-1640 medium and fixed in medium containing 2% glutaraldehyde (v/v) and 20 mM Hepes (v/v) on ice for 2 hr. Cells were washed in 0.1 M cacodylate buffer containing 20 mM calcium chloride (w/v). Cells were post-fixed with 1% osmium tetroxide in 25 mM cacodylate buffer (w/v) containing 1.5% potassium ferrocyanide (w/v) for 2 hr. on ice. Samples were dehydrated through an ethanol series, transferred to propylene oxide and embedded in Embed 800 (Electron Microscopy Sciences, PA, U.S.A.). The sections were stained with uranyl acetate/lead citrate and observed with a Hitachi 600 microscope at 75 kv.

Analysis of Cholera Toxin Binding to the H9 Human Lymphoid Cell Line Following Three Days Treatment with NB-DNJ or NB-DGJ:

Methods: Cells were maintained in logarithmic phase growth in RPMI-1640 medium. Cholera toxin B chain (Sigma) was conjugated to fluorescein isothiocyanate (Sigma) and flow cytometric analysis was carried out by conventional procedure as described by Platt et al., *Eur. J. Biochem.* 208, 187–193 (1992). Analysis was performed on a FACScan Cytometer (Becton Dickinson, Sunnyvale, Calif., USA). Data on viable cells were collected on a four decade $\log_{10}$ scale of increasing fluorescence intensity. The data are presented as percent reduction in cholera toxin bindings sites per cell on the y-axis against compound concentration on the x-axis. The specificity of cholera toxin : cell surface binding was established by inhibiting this interaction with a one hundred fold molar excess of GMI derived oligosaccharide, Galβ GalNAcβ4(NeuAcα3)Galβ4Glcβ3Cer.

RESULTS

Figure 1:
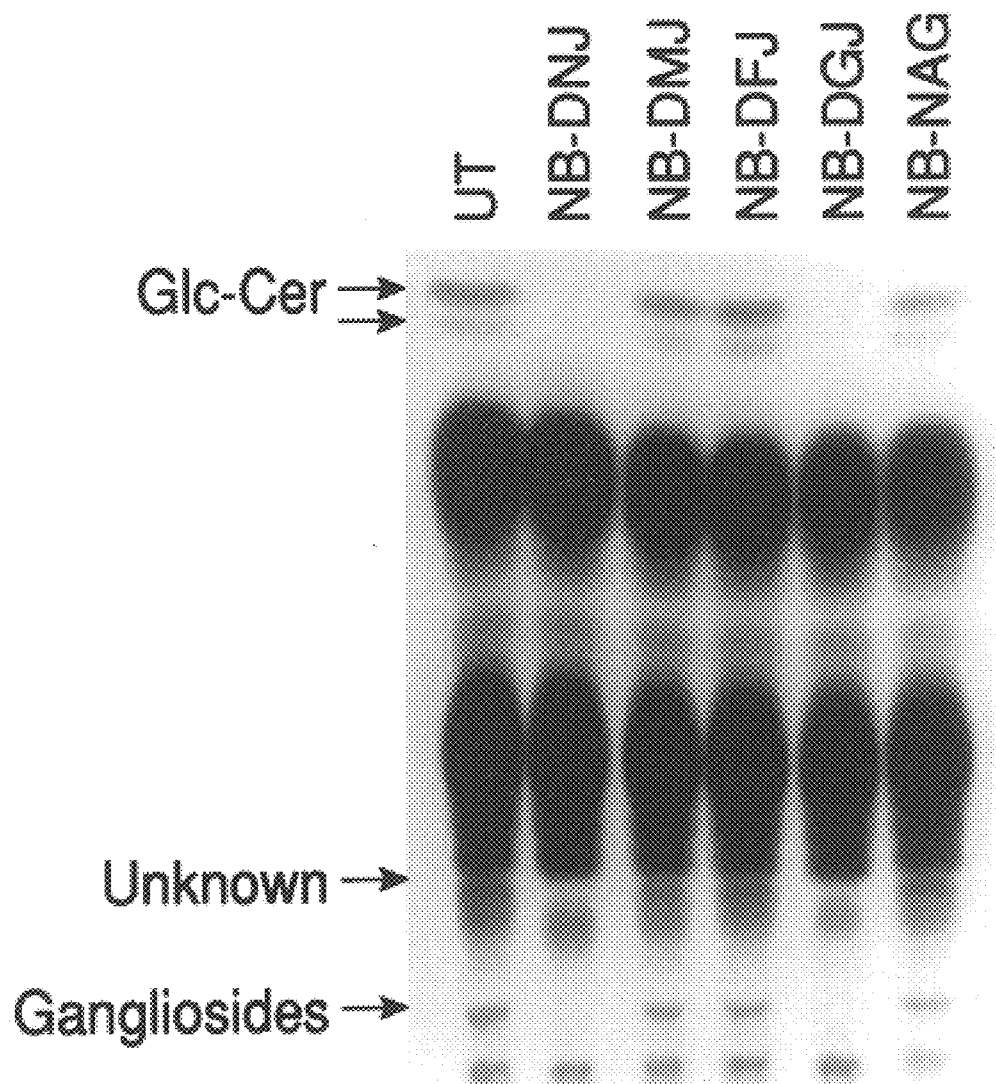
Figure 2A:
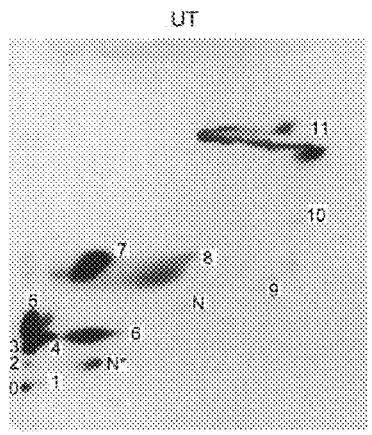
Figure 2B:
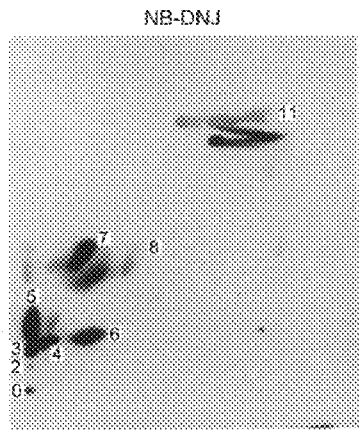
Figure 2C:
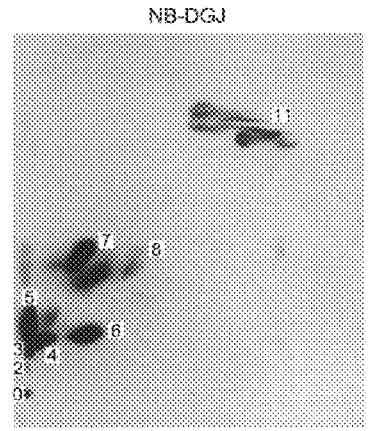
Figure 3:
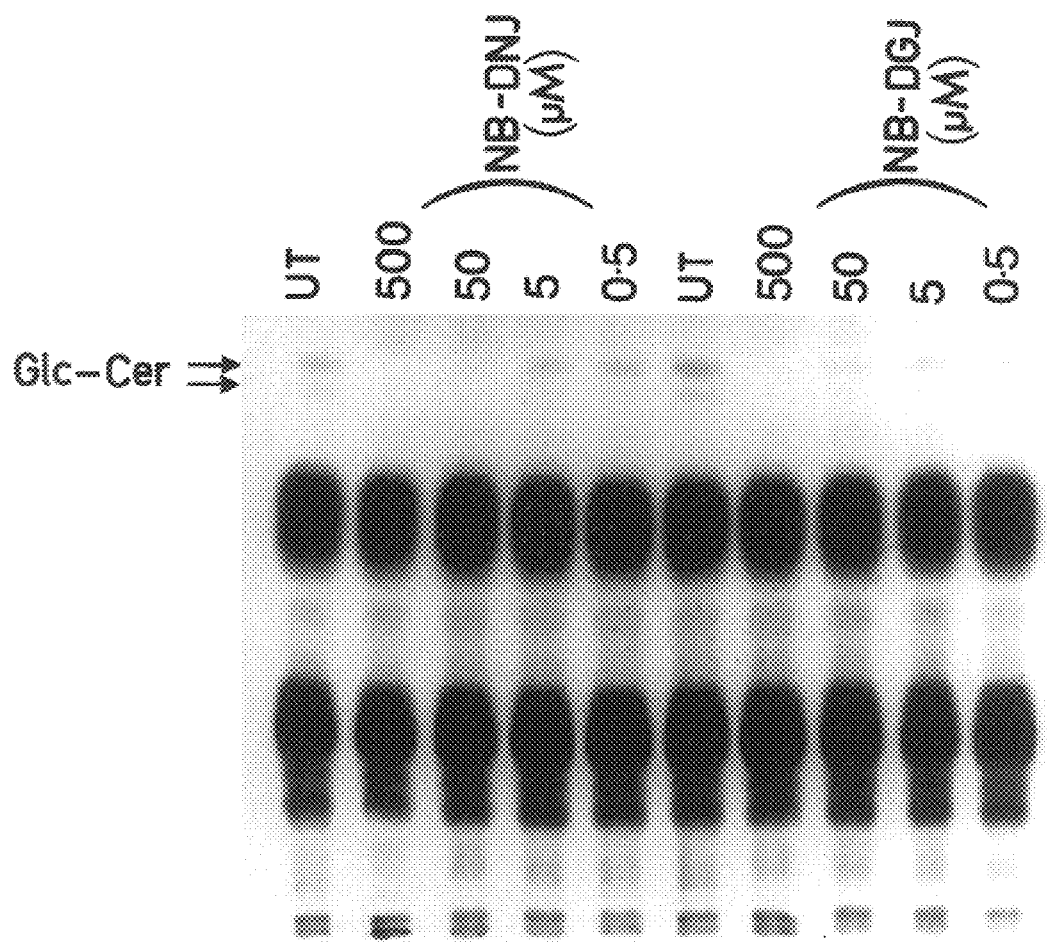

Comparison of N-alkylated Imino Sugars as Inhibitors of Glycolipid Biosynthesis:

The glucose analogue, NB-DNJ and four pyranose analogues (NB-DMJ, mannose analogue; NB-DFJ, fucose analogue; NB-DGJ, galactose analogue; and NB-NAG, N-acetylglucosamine analogue) were assessed by the above methods for their capacities to inhibit the metabolic incorporation of radiolabelled palmitate into glycolipids in HL-60 cells at a 500 µM compound concentration using 1D-TLC analysis (FIG. 1). In addition to NB-DNJ, the only analogue which specifically inhibited glycolipid biosynthesis was NB-DGJ. All other analogues were without effect. Both NB-DNJ and NB-DGJ inhibited the biosynthesis of Glc-Cer, gangliosides and an unknown lipid species in agreement with the previous observations with NB-DNJ described in copending application Ser. No. 08/061,645. To confirm that NB-DNJ and NB-DGJ had comparable effects on the complete spectrum of glycolipids in this cell line, 2D-TLC was performed to resolve further the individual glycolipid species (FIG. 2). A total depletion of glycolipid species was achieved with both 500 $\mu$M NB-DNJ and NB-DGJ. Specifically, gangliosides, the unknown lipid (N*) and both the mono and dihexaside species were absent following treatment with either compound. Phospholipid composition and relative abundance were comparable, irrespective of treatment, consistent with the previous observations in copending application Ser. No. 08/061,645 that N-alkylated imino sugars have no effect on sphingomyelin or phospholipid biosynthesis. When the two analogues were compared at a range of concentrations by 1D-TLC (FIG. 3) both analogues exhibited complete glycolipid inhibition between 50 $\mu$M and 500 $\mu$M concentrations, although partial inhibition occurred with both compounds at concentrations as low as 0.5–5 $\mu$M. Both analogues were non-cytotoxic in the dose range tested.

Figure 4A:
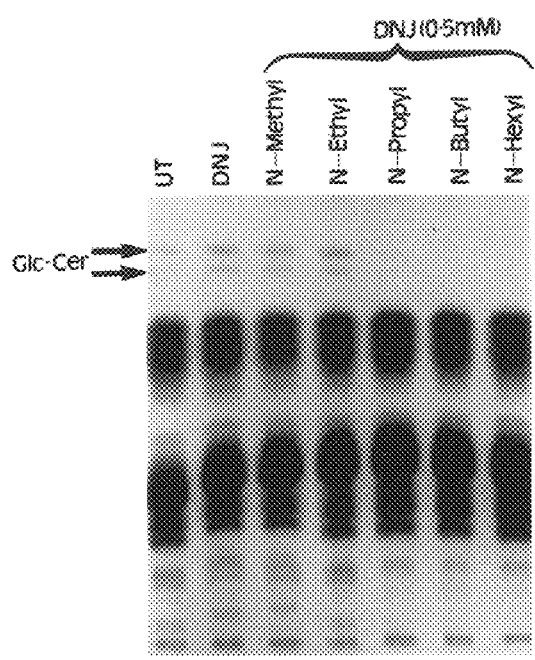
Figure 4B:
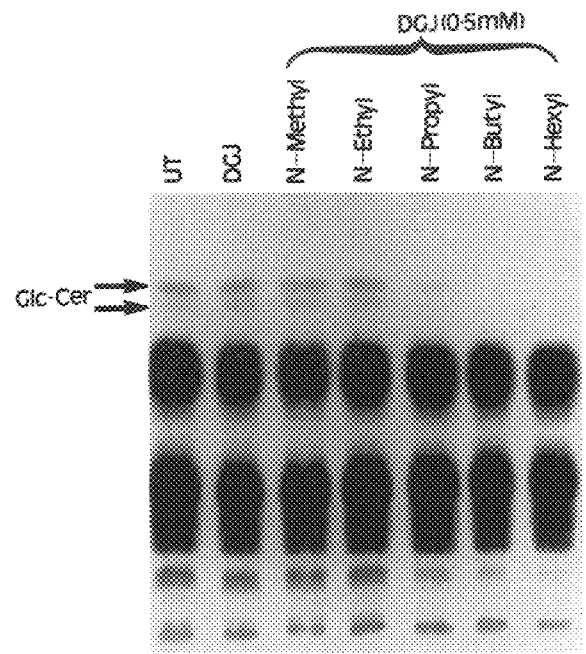

Effects of Increasing DNJ and DGJ N-alkyl Chain Length on Inhibition of Glycolipid Biosynthesis:

A series of N-alkylated DNJ and DGJ derivatives were compared for their abilities to inhibit glycolipid biosynthesis (FIGS. 4A and 4B, respectively) by 1D-TLC. The non-alkylated imino sugars and the N-methyl DNJ, N-methyl DGJ and N-ethyl DGJ had no effect on glycolipid biosynthesis. The N-propyl analogues of both parent compounds showed partial inhibitory activity, whereas the N-butyl and N-hexyl derivatives of DNJ and DGJ completely inhibited glycolipid biosynthesis, as determined by the loss of detectable Glc-Cer. These data were therefore in agreement with the data from the previous application Ser. No. 08/061,645 (where the N-methyl derivative was compared with N-butyl and N-hexyl DNJ). There is a minimal N-alkyl chain length requirement to achieve full inhibition of glycolipid biosynthesis, with butyl and hexyl being optimal.

Figure 5:
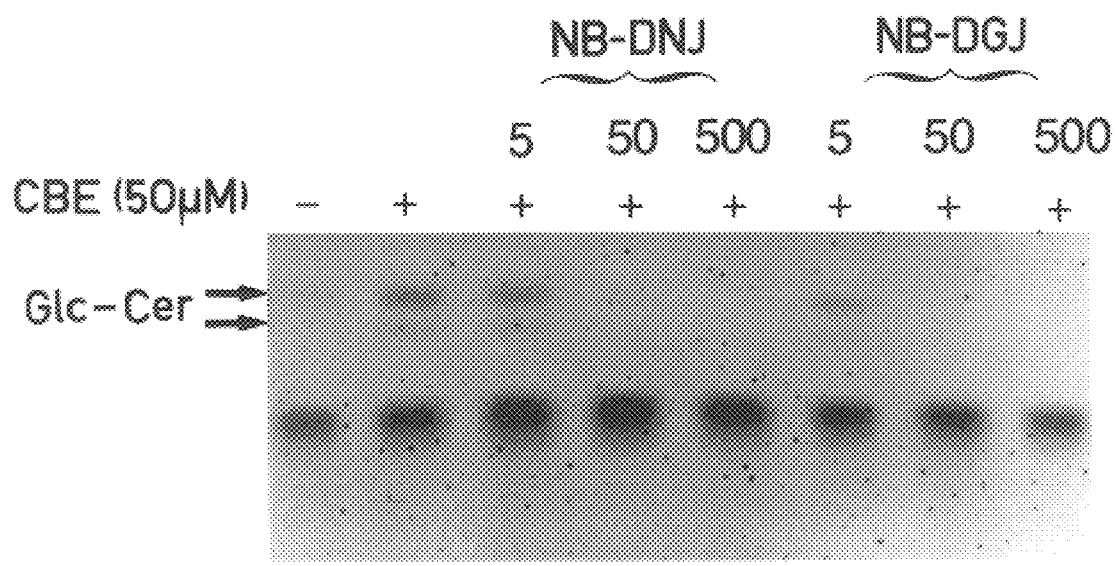
Figure 6A:
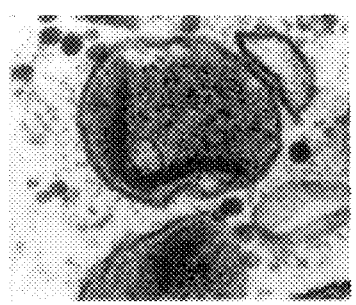
Figure 6B:
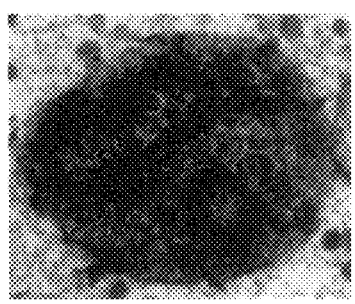
Figure 6C:
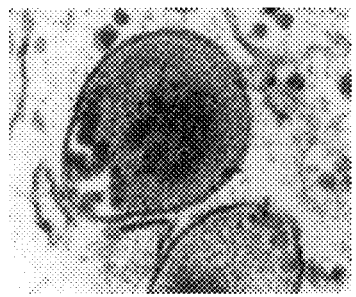
Figure 6D:
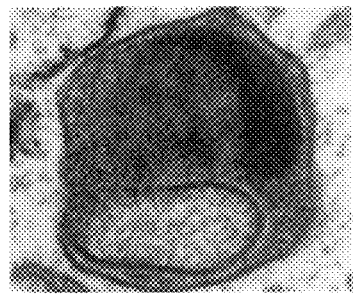
Figure 6E:
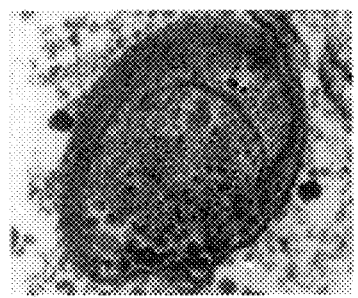
Figure 6F:
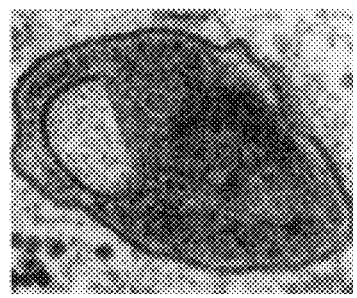
Figure 6G:
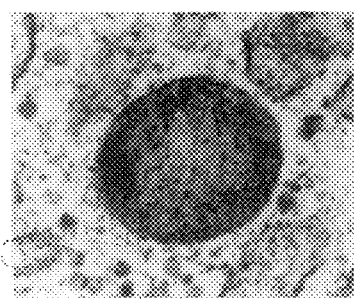
Figure 6H:
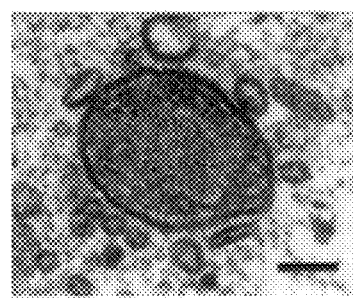

Analysis of NB-DGJ in an in Vitro Gaucher's Disease Model:

The WEHI-3B murine macrophage cell line can be induced to resemble Gaucher's cells by treatment with the irreversible glucocerebrosidase inhibitor CBE. NB-DNJ and NB-DGJ were compared in their ability to prevent the accumulation of Glc-Cer in this system (FIG. 5). Both analogues prevented CBE induced glycolipid storage in the 5–50 $\mu$M dose range. These data therefore demonstrate that NB-DGJ is as effective as NB-DNJ in preventing glycolipid storage in this in vitro Gaucher's disease model. The status of the lysosomes from cells treated with either NB-DNJ or NB-DGJ was assessed by transmission electron microscopy (FIG. 6). It was found that both analogues prevented the glycolipid accumulation observed in the lysosomes of cells treated with CBE.

Specificity of NB-DGJ for the Glycolipid Biosynthetic Pathway:

The CHO cell line is unique in that it lacks significant levels of the Golgi endomannosidase which acts to circumvent $\alpha$-glucosidase I and II inhibition [Karlsson et al., *J. Biol. Chem.* 268, 570–576 (1993); Hiraizumi et al., *J. Biol. Chem.* 268, 9927–9935 (1993)]. As a consequence, it offers an unambiguous cellular system in which to test $\alpha$-glucosidase inhibition. NB-DNJ was previously tested in this cell line expressing recombinant gp120 and it was found that it results in the maintenance of glucosylated high mannose oligosaccharides on gp120 which are fully sensitive to endo H [Karlsson et al., supra].

Figure 7:
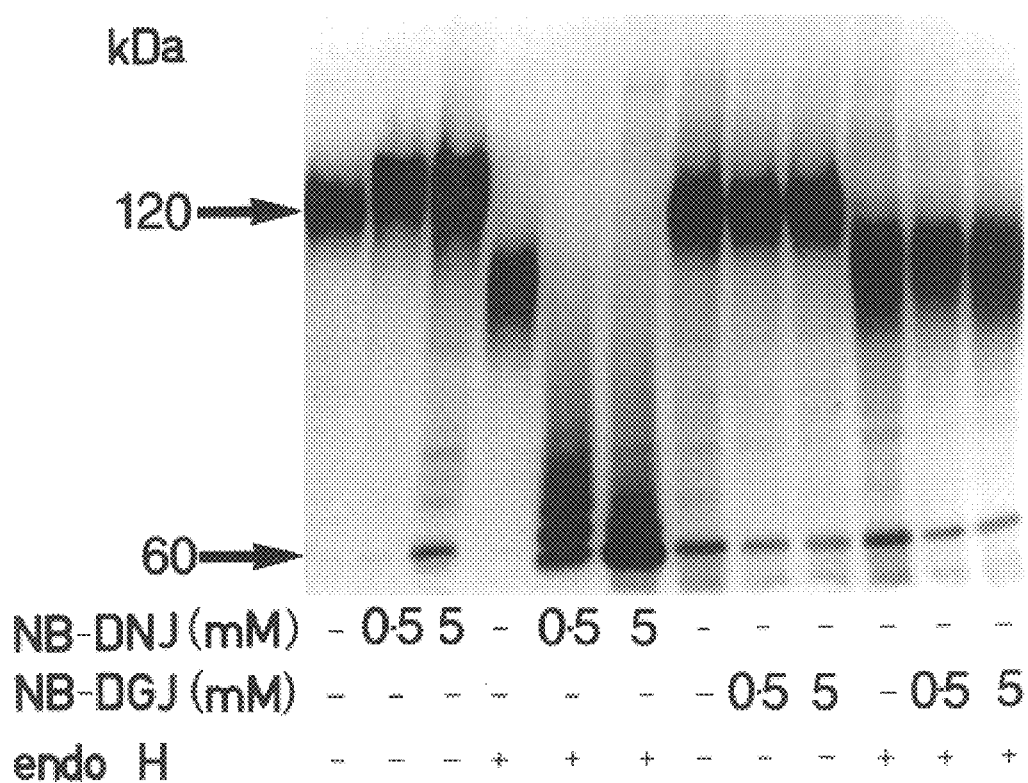

Analysis of the N-linked oligosaccharides of gp120 expressed in CHO cells was performed in the presence or absence of NB-DNJ or NB-DGJ (FIG. 7). Treatment of CHO cells with 0.5 mM or 5 mM NB-DNJ resulted in fully endo H sensitive gp120 N-linked glycans in contrast to the untreated gp120 which was partially sensitive to endo H. This partial sensitivity of untreated gp120 to endo H is because gp120 carries approximately fifty percent high mannose N-linked oligosaccharides per molecule [Mizuochi et al., *Biochem. J.* 254, 599–603 (1988); Mizuochi et al., *Biomed. Chrom.* 2, 260–270 (1988)]. However, when the galactose analogue, NB-DGJ, was tested in this system, at 0.5 mM and 5 mM concentrations, gp120 remained partially sensitive to endo H and was indistinguishable from the untreated gp120 molecules. This suggested that the galactose analogue was not acting as an inhibitor of $\alpha$-glucosidases I and II.

Figure 8A:
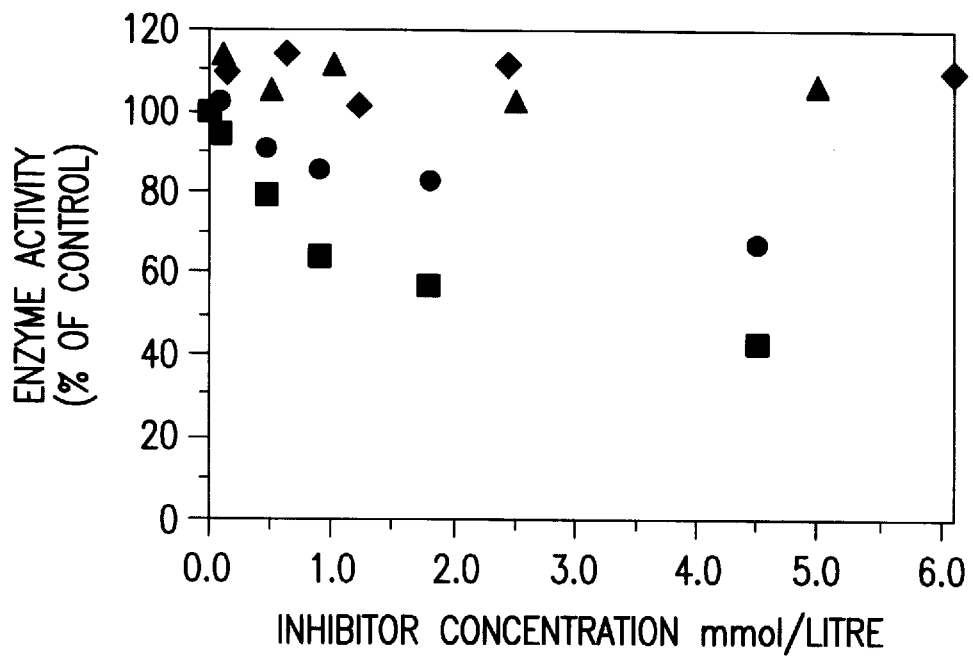
Figure 8B:
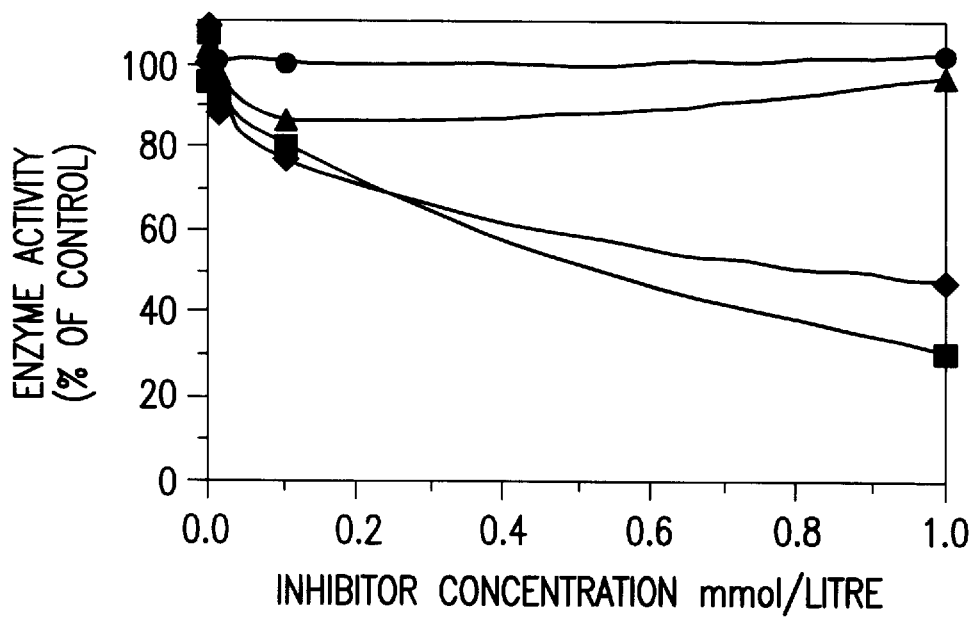
Figure 8C:
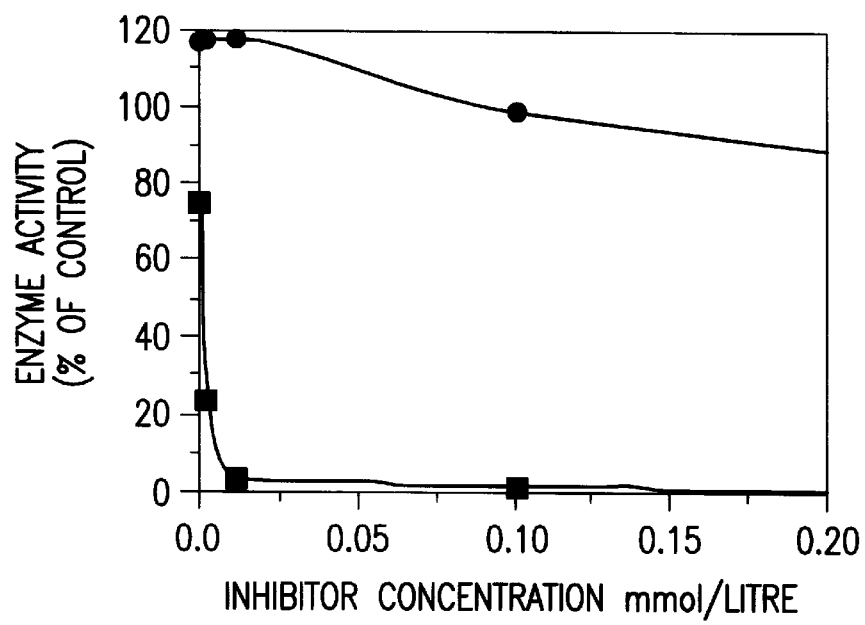

To examine the effect on endogenous glycoprotein synthesis, radiolabelled glycopeptides were isolated from treated HL-60 and murine BW5147 cells and analysed for their affinity for Con A-SEPHAROSE®. This procedure efficiently resolves tetra- and tri-antennary complex N-glycans from bi-antennary and high mannose/hybrid N-glycans [Foddy et al., *Biochem. J.* 233, 697–706 (1986)]. Addition of NB-DNJ changes the affinity of glycopeptides eluting from the Con A-SEPHAROSE® column (Table 4) as a result of processing glucosidase inhibition. Thus the proportion of unbound glycans (tetra- and tri-antennary species) decreases, and a corresponding increase is found in the proportion of high mannose/hybrid glycans that are tightly bound to Con A-SEPHAROSE® and eluted with 500 mM methylmannoside. Similar gross changes in glycopeptide composition following treatment with $\alpha$-glucosidase inhibitors are well established [Moore and Spiro, *J. Biol. Chem.* 265, 13104–13112 (1990)]. The galactose analogue, NB-DGJ, showed an unchanged glycopeptide profile by Con A-SEPHAROSE® chromatography (Table 4). To confirm these data, glucosidase inhibition was measured directly in vitro using a mixture of purified $\alpha$-glucosidases I and II (FIG. 8). Whereas NB-DNJ inhibited glucosidase I and II with an $IC_{50}$ of 0.36 $\mu$M, NB-DGJ was only weakly inhibitory ($IC_{50}$ of 2.13 mM, Table 5). These data provide substantial evidence that in both in vitro $\alpha$-glucosidase assays and in intact cellular system assays NB-DGJ does not inhibit N-linked oligosaccharide processing.

DNJ and its N-alkylated derivatives are inhibitors of the purified lysosomal glucocerebrosidase enzyme required for the cleavage of Glc-Cer to glucose and ceramide [Osiecki-Newman et al., *Biochim. Biophys. Acta.* 915, 87–100 (1987)]. In recent tests with the in vitro Gaucher's disease model in co-pending application Ser. No. 08/061,645, it was observed that WEHI-3B cells incubated in the absence of CBE but in the presence of NB-DNJ accumulated Glc-Cer. It was therefore apparent that the N-butyl derivative of DNJ was also acting as an inhibitor of glucocerebrosidase in a cellular environment. The inhibitory activity of NB-DNJ and NB-DGJ was therefore directly measured to investigate quantitatively their capacities to inhibit human placental glucocerebrosidase (Table 5). NB-DNJ provided moderate inhibition of catalysis with an $IC_{50}$ of 0.52 mM while NB-DGJ did not inhibit enzyme activity even at the highest concentration tested (1 mM). In terms of percent enzyme inhibition achieved with the two analogues, 1 mM NB-DNJ resulted in 90% inhibition while 1 mM NB-DGJ was non-inhibitory (FIG. 8), thereby further confirming the advantageous and unexpected selective inhibitory activity of NB-DGJ compared to that of NB-DNJ.

Inhibition of UDP-glucose:N-acylsphingosine Glucosyltransferase:

The determination of transferase activity using rat brain or mouse macrophage tissue cultured cells followed saturation kinetics for both exogenously added ceramide acceptor and UDP-glucose donor. Under these conditions both N-butylated DNJ and DGJ were moderate inhibitors of glucose transfer, ($IC_{50}$ 2.95 mM and 60.88 mM, respectively, Table 5) whereas their unmodified parent homologues were not inhibitory at the highest concentration tested 6.1 and 5.0 mM, respectively, FIG. 8).

Analysis of Cholera Toxin Binding to the H9 Human Limphoid Cell Line Treated with NB-DGJ:

The activity of the representative N-butyl deoxygalactonojirimycin (NB-DGJ) for inhibiting the surface expression of glycolipid receptors for bacteria and bacterial toxins was illustrated by subjecting H9 cells to cholera toxin binding sites in the presence of varying concentrations of the NB-DGJ. As a specific probe, advantage was taken of the GM1 binding specificity of the cholera toxin B chain [van Heyningen, *Nature* 249, 415–417 (1974); Karlsson, *Ann. Rev. Biochem.* 58, 309–350 (1989)]. The binding of cholera toxin to H9 cells cultured in the presence of NB-DGJ was reduced by approximately 70% (FIG. 11). This was consistent with the loss of GM1 from the cell surface and provided further evidence for the inhibition of glycolipid biosynthesis by NB-DGJ, even though by comparison it was less than the approximately 90% reduction (FIG. 11) obtained with the N-butyl deoxynojirimycin (NB-DNJ). These results demonstrate that the imino sugar derivatives have use as antimicrobial agents by inhibiting the surface expression of glycolipid receptors for bacteria and bacterial toxins as shown in Tables 1 and 2, respectively.

TABLE 1

GLYCOSPHINGOLIPID RECEPTORS FOR BACTERIAL CELLS

| Microorganism | Target Issue | Presumed Specificity |
|---|---|---|
| E. coli | Urinary | Galα4Galβ |
| E. coli | Urinary | GlcNAcβ |
| Propionibacterium | Skin/Intestine | Galβ4Glcβ |
| Several bacteria | Diverse | Galβ4Glcβ |
| Streptococcus pneumoniae | Respiratory | GlcNAcβ3Gal |
| E. coli CFA/I | Intestine | NeuAcα8 |
| E. coli | Urinary | NeuAcα3Gal |
| E. coli | Intestine | NeuGcα3Galβ4GlcβCer GalNAcβ4(NeuAcα3)-Galβ4GlcβCer |
| Staphylococcus saprophyticus | Urinary | Galβ4GlcNAc |
| Actinomyces naeslundi | Mouth | Galβ, GalNAcβ, Galβ3GalNAcβ, GalNacβ3Galβ |
| Pseudomonas | Respiratory | GalNAcβ4Gal |
| Neisseria gonorrhoeae | Genital | Galβ4Glcβ NeuAcα3Galβ4GlcNAc |

TABLE 2

GLYCOSPHINGOLIPID RECEPTORS FOR BACTERIAL TOXINS

| Microorganism | Toxin | Target Tissue | Presumed Receptor Sequence |
|---|---|---|---|
| Vibrio cholerae | Cholera toxin | Small Intestine | Galβ3GalNAcβ4-(NeuAcα3)Gal-β4GlcβCer |

TABLE 2-continued

GLYCOSPHINGOLIPID RECEPTORS FOR BACTERIAL TOXINS

| Microorganism | Toxin | Target Tissue | Presumed Receptor Sequence |
|---|---|---|---|
| E. coli | Heat-labile toxin | Intestine | Galβ3GalNAcβ4-(NeuAcα3)Gal-β4GlcβCer |
| Clostridium tetani | Tetanus toxin | Nerve | Galβ3GalNAcβ4-(NeuAcα8Neu-Acα3)Galβ4Glc-βCer |
| Clostridium botulinum | Botulinum toxin A and E | Nerve Membrane | NeuAcα8NeuAcα-3Galβ3GalNAcβ-4(NeuAcα8Neu-Acα3)Galβ4Glc-βCer |
| Clostridium botulinum | Botulinum toxin B, C and F | Nerve Membrane | NeuAcα3Galβ3-GalNAβ4(Neu-Acα8NeuAcα3)-Galβ4GlcβCer |
| Clostridium botulinum | Botulinum toxin B | Nerve Membrane | GalβCer |
| Clostridium perfringens | Delta toxin | Cell lytic | GalNAcβ4-(NeuAcα3)Galβ-4GlcβCer |
| Clostridium difficile | Toxin A | Large Intestine | Galα3GalβGlc-NAcβ3Galβ4-GlcβCer |
| Shigella dysenteriae | Shiga toxin | Large Intestine | Galα4GalβCer Galα4Galβ4Glc-GlcNAcβ4Glc-NAc |
| E. coli | Vero toxin or Shiga-like toxin | Intestine | Galα4Galβ4-GlcβCer |

TABLE 3

HERIDITARY GLYCOLIPID STORAGE DISORDERS

| Disease | Lipid Accumulation | Enzyme Defect |
|---|---|---|
| Gaucher's | Glucocerebroside | Glucocerebroside-β-glucosidase |
| Ceramide Lactoside Lipidosis | Ceramide Lactoside | Ceramidelactoside-β-galactosidase |
| Fabry's | Ceramide Trihexoside | Ceramidetrihexoside-α-galactosidase |
| Tay-Sach's | Ganglioside GM2 | Hexosaminidase A |
| Sandhoff's | Globoside and GM2 | Hexosaminidase A and B |
| General Gangliosidosis | Ganglioside GM1 | β-Galactosidase |
| Fucosidosis | H-isoantigen | α-Fucosidase |
| Krabbe's | Galactocerebroside | Galactocerebroside-β-galactosidase |
| Metrachromatic Leukodystrophy | Sulfatide | Sulfatidase |

TABLE 4

EFFECT OF IMINO SUGAR ANALOGUES ON OLIGOSACCHARIDE BIOSYNTHESIS

| Cell line | Treatment | Tetra- & Tri-antennary | Bi-antennary | Oligo-mannose & hybrid | Total $^3$H-mannose recovered (cpm) |
|---|---|---|---|---|---|
| HL-60 | untreated | 28.3 | 18.7 | 53.0 | 666918 |
| | NB-DNJ | 19.5 | 20.0 | 60.5 | 913095 |
| | NB-DGJ | 28.1 | 17.7 | 54.2 | 844322 |

TABLE 4-continued

EFFECT OF IMINO SUGAR ANALOGUES ON OLIGOSACCHARIDE BIOSYNTHESIS

| Cell line | Treatment | Tetra- & Tri-antennary | Bi-antennary | Oligo-mannose & hybrid | Total $^3$H-mannose recovered (cpm) |
|---|---|---|---|---|---|
| BW5147 | untreated | 46.1 | 5.6 | 48.3 | 476527 |
|  | NB-DNJ | 26.8 | 4.9 | 68.3 | 686026 |
|  | NB-DGJ | 40.4 | 7.2 | 52.4 | 706873 |

Cells were radiolabelled for 4 hr. with [$^3$H]-mannose in the presence or absence of compounds as shown above. Washed cells were exhaustively digested with Pronase® enzyme and resultant glycopeptides fractionated by Con A-SEPHAROSE® chromatography as described hereinbefore. The percentage of radiolabelled glycopeptides that were non-bound (complex tetra- and tri-antennary N-glycans), eluted with 10 mM methylglucoside (complex bi-antennary N-glycans), or further eluted with 500 mM methylmannoside (oligomannose and hybrid N-glycans) were calculated from estimations of radioactivity recovered from pooled eluates.

TABLE 5

CONCENTRATIONS OF IMINO SUGAR ANALOGUES REQUIRED FOR THE INHIBITION OF GLYCOLIPID AND GLYCOPROTEIN METABOLISING ENZYMES

| | Compound IC$_{50}$ values | | | |
|---|---|---|---|---|
| Enzyme | DNJ | NB-DNJ | DGJ | NB-DGJ |
| UDP-glucose:N-acylsphingosine glucosyltransferase | —† | 2.95 mM | —† | 60.88 mM |
| β-glucocerebrosidase | 2.43 mM | 0.52 mM | —* | —* |
| α-glucosidase I and II | nd | 0.36 µM | nd | 2.13 mM |

*not inhibitory at 1 mM concentrations of compound.
† not inhibitory at the highest concentrations tested (see FIG. 8)
nd not determined TABLE 5-continued CONCENTRATIONS OF IMINO SUGAR ANALOGUES REQUIRED FOR THE INHIBITION OF GLYCOLIPID AND GLYCOPROTEIN METABOLISING ENZYMES

| | Compound IC$_{50}$ values | | | |
|---|---|---|---|---|
| Enzyme | DNJ | NB-DNJ | DGJ | NB-DGJ |

Enzymes were assayed according to procedure described hereinbefore using concentrations of analogues shown in FIG. 8. The data from FIG. 8 were plotted on a logarithmic scale for accurate estimations of IC$_{50}$ values, shown above.

In addition to their use as inhibitors of glycolipid biosynthesis in cells, the inhibitory agents described herein also can be used for administration to patients afflicted with glycolipid storage defects by conventional means, preferably in formulations with pharmaceutically acceptable diluents and carriers. These agents can be used in the free amine form or in their salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human daily dosage would normally range from about one to about 100 milligrams of the active compound. The preferable route of administration is orally in the form of capsules, tablets, syrups, elixirs and the like, although parenteral administration also can be used. Suitable formulations of the active compound in pharmaceutically acceptable diluents and carriers in therapeutic dosage form can be prepared by reference to general texts in the field such as, for example, *Remington's Pharmaceutical Sciences*, Ed. Arthur Osol, 16th ed., 1980, Mack Publishing Co., Easton, Pa., U.S.A.

Various other examples will be apparent to the person skilled in the art after reading the present disclosure without departing from the spirit and scope of the invention. It is intended that all such other examples be included within the scope of the appended claims.

What is claimed:

1. N-alkyldeoxygalactonojirimycin in which the alkyl is butyl.

* * * * *

UNITED STATES PATENT AND TRADEMARK OFFICE
CERTIFICATE OF CORRECTION

PATENT NO. : 6,291,657 B1
DATED : September 18, 2001
INVENTOR(S) : Frances M. Platt et al.

It is certified that error appears in the above-identified patent and that said Letters Patent is hereby corrected as shown below:

Column 2,
Line 34, after "the" insert -- bacteria --.

Column 11,
Line 40, "Issue" should read -- Tissue --.

Signed and Sealed this

Sixteenth Day of April, 2002

Attest:

JAMES E. ROGAN
Attesting Officer
Director of the United States Patent and Trademark Office